(12) United States Patent
Wang et al.

(10) Patent No.: US 8,178,521 B2
(45) Date of Patent: May 15, 2012

(54) CEFAZOLIN SODIUM PENTAHYDRATE CRYSTAL AND ITS MOLECULAR ASSEMBLY PREPARATION METHOD

(75) Inventors: Jingkang Wang, Tianjin (CN); Yuxin Qian, Shenzhen (CN); Meijing Zhang, Tianjin (CN); Jiehua Wu, Tianjin (CN); Zhan'ao Yang, Shenzhen (CN)

(73) Assignees: Tianjin University, Nankai District, Tianjin (CN); Shenzhen Gosun Pharmaceutical Co., Ltd., Futian District, Shenzhen (CN)

( * ) Notice: Subject to any disclaimer, the term of this patent is extended or adjusted under 35 U.S.C. 154(b) by 525 days.

(21) Appl. No.: 12/085,110

(22) PCT Filed: Sep. 15, 2006

(86) PCT No.: PCT/CN2006/002414
§ 371 (c)(1),
(2), (4) Date: May 15, 2009

(87) PCT Pub. No.: WO2007/056918
PCT Pub. Date: May 24, 2007

(65) Prior Publication Data
US 2009/0299056 A1    Dec. 3, 2009

(30) Foreign Application Priority Data

Nov. 16, 2005   (CN) .......................... 2005 1 0016123

(51) Int. Cl.
    C07D 501/36    (2006.01)
    C07D 501/02    (2006.01)
    C07D 501/12    (2006.01)
    C07D 501/59    (2006.01)
    A61K 31/545    (2006.01)
(52) U.S. Cl. ........................ 514/206; 540/227
(58) Field of Classification Search .................. 540/227; 514/206
    See application file for complete search history.

(56) References Cited

U.S. PATENT DOCUMENTS

| 4,104,470 A | 8/1978 | Cise et al. |
| 4,146,971 A | 4/1979 | Bornstein et al. |
| 4,898,937 A | 2/1990 | Uemura et al. |

FOREIGN PATENT DOCUMENTS
CN          1513854          7/2004

OTHER PUBLICATIONS

Sohn et al. Yakhak Hoechi (1996), 40(3), 306-310.*
Stephenson et al. International Journal of Pharmaceutics (2000), 198(2), 167-177.*
Kamat et al. Pharmaceutical Research (1988), 5(7), 426-9.*
Osawa et al. Pharmaceutical Research (1988), 5(7), 421-5.*
Koyama et al. Journal of Parenteral Science and Technology (1988), 42(2), 47-52.*
Kariyone, et al. "Cefazolin, a New Semisynthetic Cephalosporin Antibiotic." J. Antibiotics, vol. XXIII, No. 3, pp. 131-136, (1970).
International Search Report dated Jan. 4, 2007 issued in corresponding PCT Application No. PCT/CN2006/002414.
European Office Action dated Aug. 3, 2010, issued in corresponding European Patent Application No. 06775666.8.
Chinese Office Action issued in corresponding Chinese Patent Application No. 200510016123.5.
J. Wu et al., "Solubility of Cefazolin Sodium Pentahydrate in Aqueous 2-Propanol Mixtures.", *Journal of Chemical Engineering Data*, vol. 50, No. 3, 2005, pp. 980-982.
Mino R. Caira, "Crystalline Polymorphism of Organic Compounds.", *Topics in Current Chemistry*, Springer Verlag, Berlin, DE, vol. 198, 1998, pp. 163-208.

* cited by examiner

*Primary Examiner* — Kahsay T Habte
(74) *Attorney, Agent, or Firm* — Kenyon & Kenyon LLP

(57) ABSTRACT

The present invention relates to cefazolin sodium pentahydrate crystal and a method for assembly and preparation of the crystal molecule. The cefazolin sodium pentahydrate crystal molecule contains five water molecules, orthorhombic system, space group of C222(1), in which sodium ion is bonded to the cefazolin molecule with a coordinate bond. The method for assembly and preparation of cefazolin sodium pentahydrate crystal molecule are: adding a solvent to a reactor equipped with a jacket, adding cefazolin acid and a sodium salt, heating until the reaction solution is clear, stirring continuously, adjusting pH, upon the completion of the reaction, transferring the liquid into a jacketed crystallizer, adding crystal seeds or nucleating spontaneously, controlling cooling, slowly adding a antisolvent. The particle size of cefazolin sodium pentahydrate crystal according to the present invention is adjustable, and the distribution of particle size is concentrated, the product has good flowability, smooth surface, high crystallinity, good stability, and rapid dissolving rate.

15 Claims, 4 Drawing Sheets

CEFAZOLIN SODIUM PENTAHYDRATE CRYSTAL AND ITS MOLECULAR ASSEMBLY PREPARATION METHOD

CROSS-REFERENCE TO RELATED APPLICATIONS

This application is a 371 of PCT International Application No. PCT/CN2006/002414, filed on Sep. 15, 2006, which claims priority to Chinese Patent Application No. 200510016123.5, filed on Nov. 16, 2005, hereby incorporated by reference.

FIELD OF INVENTION

The present invention belongs to crystallization technology field, particularly to the structure of cefazolin sodium pentahydrate crystal molecule and a method for assembly and preparation of the same.

BACKGROUND OF THE INVENTION

Cefazolin sodium, its full name is: Monosodium (6R,7R)-3-[[(5-methyl-1,3,4-thiadiazol-2-yl)thio]methyl]-7-(1H-tetrazol-1-yl)acetyla mino]-8-oxo-5-thia-1-azabicyclo[4.2.0]-oct-2-ene-2-carboxylate, its chemical formula is $C_{14}H_{14}N_8O_4S_3$, its pentahydrated compound has a structure formula as shown in FIG. 1, being white or near white crystalline powder, with a molecular weight of 566.57, and a theoretical water content of 15.9%; it is freely soluble in water, slightly soluble in methanol and ethanol, and practically insoluble in isopropanol, acetone, chloroform, dichloromethane and ethyl acetate; it has no fixed melting point, and its decomposition temperature is 193±2° C.

Cefazolin sodium is the first generation of broad-spectrum antibiotic, it exhibits excellent antibacterial activity to Gram-positive coccus, except enterococcus, methicillin-resistant staphylococcus. *Streptococcus pneumoniae* and *streptococcus haemolytica* are highly sensitive to this product. *Corynebacterium diphtheriae, bacillus anthracis*, listeria and clostridium are also very sensitive to this product. This product has good antibacterial activity to partial *E.coli, proteus mirabilis* and *klebsiella pneumoniae*, but has low antibacterial activity to actistaphylococcus. Typhoid bacillus, shigella and neisseria are sensitive to this product, but other enterobacteriaceae, acinetobacter and *P. aeruginosa* are resistant to this product. PPNG (Penicillinase-Producing *Neisseria gonorrheae*) is resistant to this product. *Haemophilus influenzae* only exhibits intermediate sensitivity. With the enhancement of the standard of living of common people and domestic production level, recently, the demand of cefazolin sodium has been increased continuously.

At present, it has been known that cefazolin sodium has 4 crystalline forms, i.e., α-crystal, β-crystal, γ-crystal, and amorphous crystal forms, in which α-crystal of cefazolin sodium is present in needle crystal, with a specific rotation of −20°--25°, and absorbance index ($E_{1cm}^{1\%}$) of 272-292. U.S. Pat. No. 4,104,470 describes a method for the preparation of monohydrated cefazolin sodium. U.S. Pat. No. 4,146,971 describes a method for the preparation of a rapidly dissolving cefazolin sodium crystal. U.S. Pat. No. 4,898,937 describes that cefazolin sodium is placed in moisture environment to obtain α-crystals of cefazolin sodium. Above methods are not suitable for bulk production, and the resulting products are easily dehydrated to convert into other crystal forms.

CN1513854A discloses a method for preparing chelated cefazolin sodium. The examples 1-5 and 6-8 of the invention describe a method to prepare chelated cefazolin sodium from cefazolin acid by, after salt formation, adjusting pH in isopropanol solvent or a mixed solvent. The solvent means isopropanol or isopropanol+acetone, isopropanol+dichloromethane, isopropanol+ethyl acetate. In these examples, the preparation of chelated cefazolin sodium comprises following steps: 1) salt formation of cefazolin acid; 2) pH regulation; 3) addition of solvent. This invention has following problems: 1) long reaction time; 2) small particle size of the product, it has been proved in practice that the average particle size of the product obtained in the examples of this invention is about 15 microns; 3) the chelated cefazolin sodium crystal obtained in the examples of this invention is a monoclinic crystal, with a space group of P21.

SUMMARY OF THE INVENTION

One embodiment of the invention is the cefazolin sodium pentahydrate crystal, characterized in that the crystal molecule contains five water molecules, orthorhombic system, space group of C222(1), in which sodium ion is bonded to the cefazolin molecule with a coordination bond.

Another embodiment of the invention encompasses a method for preparing cefazolin sodium pentahydrate crystal comprising: adding 1-20 parts of a solvent to a reactor equipped with a jacket; adding 1 part of cefazolin acid and sodium salt in a molar ratio of about 1:1 to provide a reaction solution; heating until the reaction solution is clear; adjusting pH to 3-9; upon the completion of the reaction, transferring the liquid to a crystallizer equipped with a jacket; cooling in water bath; adding crystallization additives; holding for 0.3-4 hours at 0.8-2.5 atmospheric pressure; cooling in the temperature range of 0° C.-70° C., adding 3-15 parts of an anti-solvent, filtering, washing with a detergent, and drying to provide cefazolin sodium pentahydrate.

DETAILED DESCRIPTION OF THE INVENTION

Figure 1:
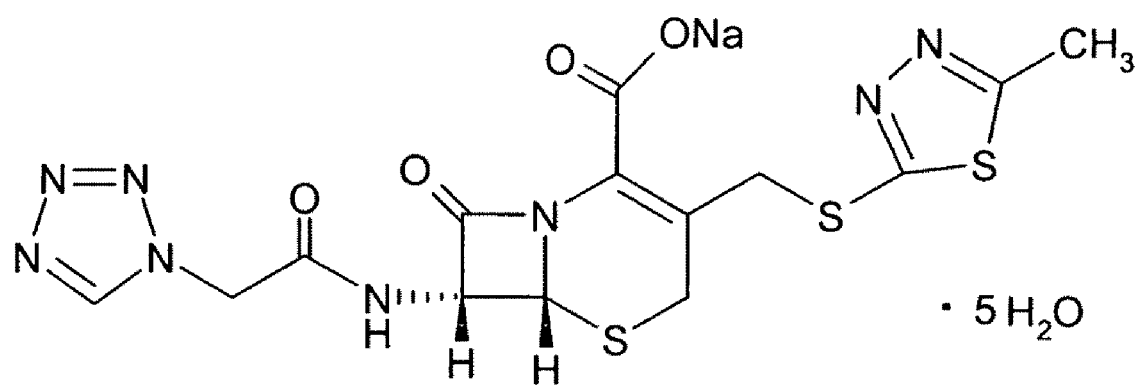
FIG. 1: Skeleton symbol of molecular structure of cefazolin sodium pentahydrate.

The present invention provides a novel cefazolin sodium pentahydrate crystal and a method for assembly and preparation of the crystal molecule. The structure of the novel cefazolin sodium pentahydrate crystal according to the present invention is: the crystal molecule contains five water molecules, orthorhombic system, space group of C222(1), in which sodium ion is bonded to the cefazolin molecule with a coordinate bond.

Cefazolin sodium pentahydrate according to the present invention is characterized that one sodium ion and N3 in two cefazolin molecules and oxygen in four water molecules form sexadentate, another sodium has weak bond action with O3W and O6W, cefazolin and water molecule, and water molecules are linked with hydrogen bond to maintain a stable arrangement under molecule crystalline state.

The assembly and preparation method of cefazolin sodium pentahydrate crystal molecule according to the present invention are described as follows:

To a jacketed reactor is added 1-20 parts (preferably 1-10 parts) of crystallizing solvent, 1 part of cefazolin acid and sodium salt with molar ratio of 1:1 (generally 2:1-1:2, preferably 1.3:1-1:1.3), heated and stirred until the solution was clear, agitated for 10-60 minutes (preferably 20-40 minutes), pH is adjusted to be 3-9 (preferably pH 4-7). Upon the completion of the reaction, the liquid is transferred to a crystallizer equipped with a jacket, cooled by controlling water bath, crystallized with a crystallizing agent and hold for 0.3-4 hours (preferably 0.5-2 hours) at 0.8-2.5 atmospheric pressure (preferably 1.1-2 atmospheric pressure). The preferred cooling region is controlled in the range of 0° C.-70° C. (preferably 5° C.-50° C.), in the course is slowly added 3-15 parts (preferably 5-10 parts) of a precipitating agent.

The crystallizing solvents used in the method for preparing a crystal according to the present invention for are preferably selected from the mixtures of water and organic solvents preferably selected from acetone, dichloromethane, chloroform, methanol, ethanol, isopropanol, butanol, ethyl ether or ethyl acetate, butyl acetate, or mixtures thereof. The water content in the crystallizing solvent is >15%.

The sodium salts used in the method for preparing a crystal according to the present invention are preferably selected from one of sodium carbonate, sodium hydroxide, sodium acetate, trihydrated sodium acetate, sodium isocaprylate, sodium methoxide, sodium bicarbonate, and sodium ethoxide, or a mixture thereof.

The precipitating agents are oxygen-containing fatty hydrocarbons derivatives or mixtures thereof, mainly including fatty acids, aliphatic alcohols or ketones as well as their dibasic or polybasic mixtures. For example, the fatty acids are formic acid or acetic acid, and the like; the aliphatic alcohols are methanol, ethanol, n-propanol, isopropanol, n-butanol or isobutanol, and the like; the ketones are acetone, isobutyl ketone or methyl ethyl ketone, and the like. The preferred precipitating agents are ethanol, isopropanol, n-butanol, acetone, isobutyl ketone or acetic acid, and the like. The preferred dibasic mixed solvents as precipitating agents include: methanol and isopropanol, acetone and ethanol, acetone and acetic acid, isobutyl ketone and isopropanyl, n-propanol and formic acid, and the like, in a ratio of 20:1 to 1:20, preferably 10:1 to 1:10.

The crystallizing agents used in the method for preparing a crystal according to the present invention are amino acids compounds, preferably lysine, serine, methionine, leucine, more preferably lysine, serine. The amount of the crystallizing agents is preferably 0.1-0.5 ppm, more preferably 0.2-0.4 ppm.

The prepared cefazolin sodium pentahydrate crystal molecule according to the present invention can be further subjected to post-treatments, including: filtering, washing, drying and so on. The product can be selectively washed with a detergent. The washed product is dried in air or vacuum at 5-80° C. for 0.5-8 hours to finally give a product of cefazolin sodium pentahydrate.

The detergents are preferably oxygen-containing fatty hydrocarbons derivatives or mixtures thereof, mainly including fatty acids, aliphatic alcohols or ketones as well as mixtures of two or more solvents. For example, the fatty acids are formic acid or acetic acid, and the like; the aliphatic alcohols are methanol, ethanol, n-propanol, isopropanol, n-butanol or isobutanol, and the like; the ketones are acetone, isobutyl ketone or methyl ethyl ketone, and the like.

X-ray powder diffraction pattern showed that the cefazolin sodium pentahydrate according to the present invention possess characteristic peaks at about 4.8, 5.8, 6.3, 11.6, 13.5, 14.9, 15.9, 17.4, 18.7, 19.0, 19.6, 20.0, 20.8, 21.4, 27.3, 29.5 (degrees 2θ/) and so on.

The infrared adsorption spectrum of cefazolin sodium pentahydrate according to the present invention has characteristic absorption peaks at $3432(\pm5)cm^{-1}$, $3287(\pm5)cm^{-1}$, $1761(\pm5)cm^{-1}$, $1667(\pm5)cm^{-1}$, $1599(\pm5)cm^{-1}$, $1540(\pm5)cm^{-1}$, $1389(\pm5)cm^{-1}$, $1239(\pm5)cm^{-1}$, and $1184(\pm5)cm^{-1}$ and so on, measured by infrared spectrophotometry (Chinese Pharmacopoeia 2000 Edition 2 Section, Annex IVC).

The cefazolin sodium pentahydrate according to the present invention (which is prepared by adding water into a solution containing 0.1 g per 1 ml) has a pH value of 4.8-6.3, and a water content of 13.0-16.0%, measured by Chinese Pharmacopoeia 2000 Edition 2 Section, Annex VIII M, First Method A.

DSC pattern showed that the temperature elevating rate Of cefazolin sodium pentahydrate according to the present invention is 5° C. $min^{-1}$, the product has two dehydration peaks, the dehydration temperature is $93(\pm5)0°$ C. and $98(\pm5)°$ C.; cefazolin sodium directly decomposes without a melting adsorption peak, the decomposition temperature is $193(\pm5)°$ C., and the decomposition heat is $-56(\pm5)kJ/mol$.

The particle size of cefazolin sodium pentahydrate according to the present invention is adjustable (main size is from 17 to 500 um) by altering stirring rotation speed and fluid adding rate, and the distribution of particle size is concentrated, the surface of the particles is smooth, the product exhibits excellent flowability, high crystallinity, good stability (it is identified by State Food and Drug Administration to have a expiry date of 24 months, whereas the expiry date of commercial cefazolin sodium at present is 18 months), and rapid dissolving rate.

EXAMPLES

The present invention is specifically explained by following examples:

Example 1

To a glass reactor equipped with a jacket were added 100 ml ethanol solution (containing 20% water), 10.0 g cefazolin acid and 2 g sodium ethoxide, stirred until the completion of the reaction, the finishing point pH was adjusted to be 4.5, the mixture was filtered into a jacketed crystallizer, agitated for 20 minutes, cooled in water bath, added lysine and crystal seeds at about 60° C., turbidity occurred in the crystallizer, hold for 0.8 hours. To the crystallizer were slowly added isopropanol and acetone in a volume five times as much as the mixture (in which the volume ratio of acetone is 5%) at 1.1 Mpa (optionally).

The resultant was filtered, washed with methanol, dried at 30° C. for 4 hours to give cefazolin sodium pentahydrate.

The structure of the single crystal of the product obtained in the example was shown in table 1.

In the example, ethanol can be replaced by acetone, dichloromethane, chloroform, methanol, isopropanol, butanol, ethyl ether or ethyl acetate, butyl acetate.

Example 2

To a reactor equipped with a jacket were added 5 ml isopropanol, 5 ml water, 10 g cefazolin acid and 1.2 g sodium carbonate, stirred and heated to 50° C. until the solution was clear, the finishing point pH was adjusted to be 6.5, the mixture was directly filtered into a glass crystallizer, agitated, cooled to about 33° C., added serine, turbidness occurred in the solution, hold for 1.0 hours, added anhydrous ethanol in an amount of 15 times as much as the mixture at 2 MPa, cooled to 5-15° C. and hold at the temperature for 1 hour. The resultant was filtered, the filter cake was washed with ethanol, dried at 5° C. for 8 hours to give cefazolin sodium pentahydrate.

The structure of the single crystal of the product obtained in the example was shown in table 1.

In the example, isopropanol can be replaced by methanol and isopropanol, acetone and ethanol, acetone and acetic acid, isobutyl ketone and isopropanol, n-butanol and formic acid.

Example 3

To a reactor equipped with a jacket were added 10 ml ethanol, 50 ml dichloromethane, 20 ml water, 5 g cefazolin acid and 0.9 g sodium acetate, stirred until the solution was clear, the finishing point pH was adjusted to be 7.4, the mixture was directly filtered into a glass crystallizer, agitated for 60 minutes, added dropwise about 20 ml of isopropanol and methanol mixed liquid (the amount of methanol is 3%) and methionine, turbidness occurred in the solution, hold for 4.0 hours, added isopropanol and methanol in a volume 10 times as much as the mixture at 1.5 MPa. The resultant was filtered, the filter cake was washed with acetic acid, dried at 80° C. for 0.5 hours to give cefazolin sodium pentahydrate.

The structure of the single crystal of the product obtained in the example was shown in table 1.

In the example, ethanol can be replaced by formic acid, methanol, ethanol, n-propanol, isopropanol, n-butanol, isobutanol, acetone, isobutyl ketone or methyl ethyl ketone.

TABLE 1

| No. | Example 1 | Example 2 | Example 3 |
|---|---|---|---|
| Crystal system | Orthogonal | Orthogonal | Orthogonal |
| Space group | C222(1) | C222(1) | C222(1) |
| Unit cell parameters | a = 4.7567(10)A | a = 4.8220(10)A | a = 4.8263(10)A |
| | b = 35.992(7)A | b = 36.165(7)A | b = 36.132(7)A |
| | c = 27.843(6)A | c = 28.038(6)A | c = 28.060(6)A |
| | α = 90° | α = 90° | α = 90° |
| | β = 90° | β = 90° | β = 90° |
| | γ = 90° | γ = 90° | γ = 90° |

Example 4

This example illustrates a method to identify the structure of crystals. The crystal of cefazolin sodium pentahydrate obtained in the invention is colorless transparent needle type. The crystal had a dimension of 0.46×0.16×0.07 mm, measured by X-ray unit cell diffraction experiments. Diffraction strength data were collected by means of Rigaku Rapid-II surface detector, MoKa radiation, graphic monochromator, pipe voltage, 50 kV, pipe current 90 mA, ω-scanning, scanning scopes are chi=45°, phi=30°, ω scanned from 130° to 190°; chi=45°, phi=180°, ω scanned from 0° to 159°, oscillation angle was 3°, space was 3°, 73 pictures were taken in total, independent diffraction points were 3165, observable points (>2sigma(l)) were 4566.

The structure of crystals was analyzed by computer by means of direct method (SHELXS-97). The atomic positions were obtained from the pictures. Difference Fourier method was used to acquire other non-hydrogen atoms, to correct structural parameters and to determine the kinds of atoms. The position of hydrogen atom was obtained by geometrical calculation method and difference Fourier method, reliability factor R=8.16, finally the stechiometric formula of each asymmetric unit was $C_{14}H_{13}O_4N_8S_3$, which contained 6 water positions, in total five water molecules.

Figure 3:
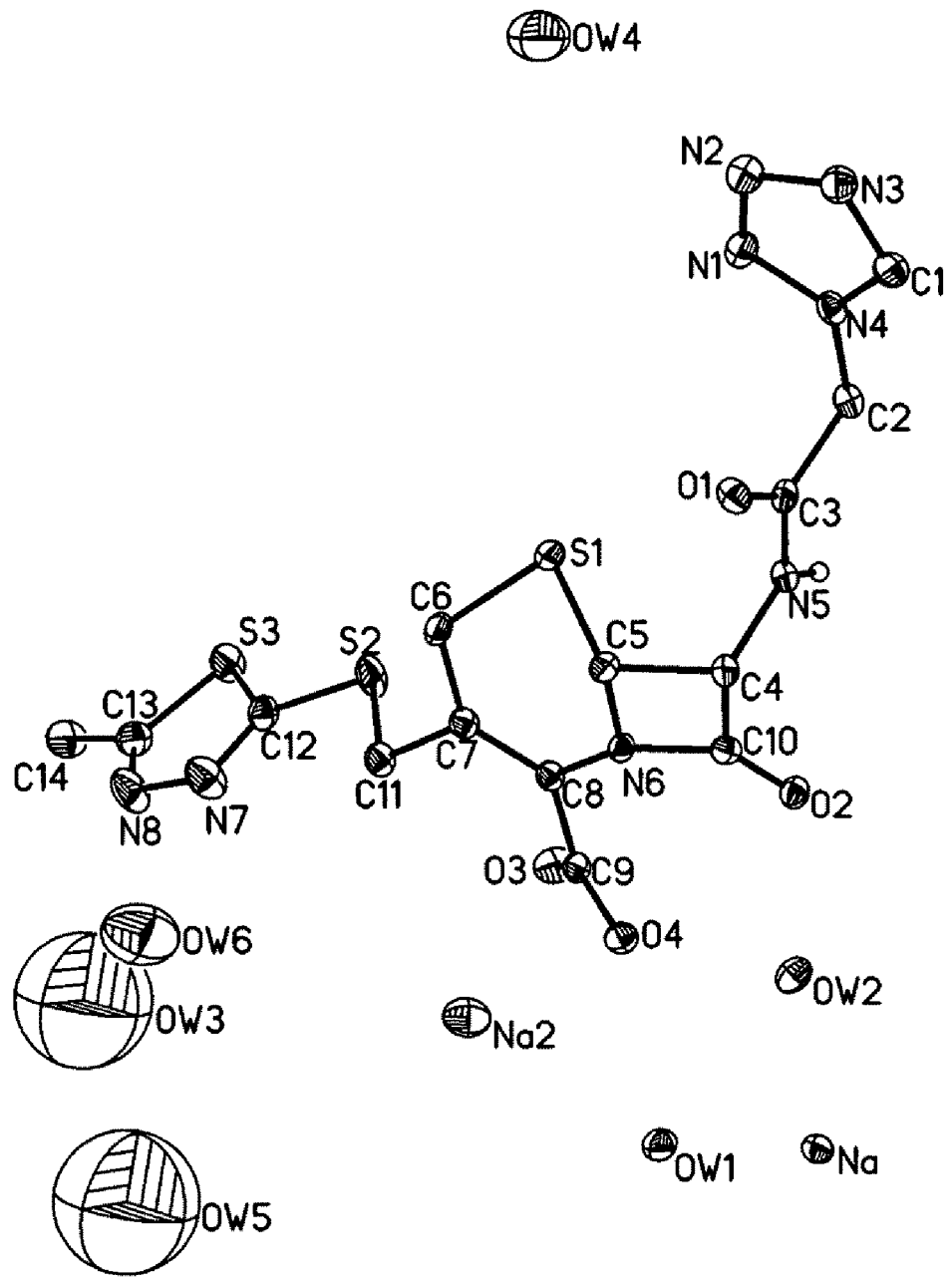
FIG. 3: Skiagraph of spatial structure of cefazolin sodium pentahydrate.

The skiagraph of spatial structure of cefazolin sodium pentahydrate molecular according to the present invention was shown in FIG. 3. One asymmetric unit in crystal state contained one cefazolin molecule, five water molecules and 2 sodium ions (the position occupation degree of each sodium ion is 0.5). Cefazolin molecules in crystal state were arranged into a tunnel cavity, water molecules and sodium ions were present in the cavity. Sodium ions together with two nitrogen atoms N3(N3') in two cefazolin molecules and four water molecules of O1W(O1W') and O2W(O2W'), respectively formed 6-coordinated hexagonal double cone, so that O1W, O2W were stable in crystal state. Another sodium and O3W and O6W exhibited weak linkage action. Cefazolin and water molecule, and water molecules were linked with hydrogen bond to maintain a stable arrangement under molecular crystal state, as shown in the chart of accumulation of molecule in the direction of a axis (FIG. 4).

Figure 2:
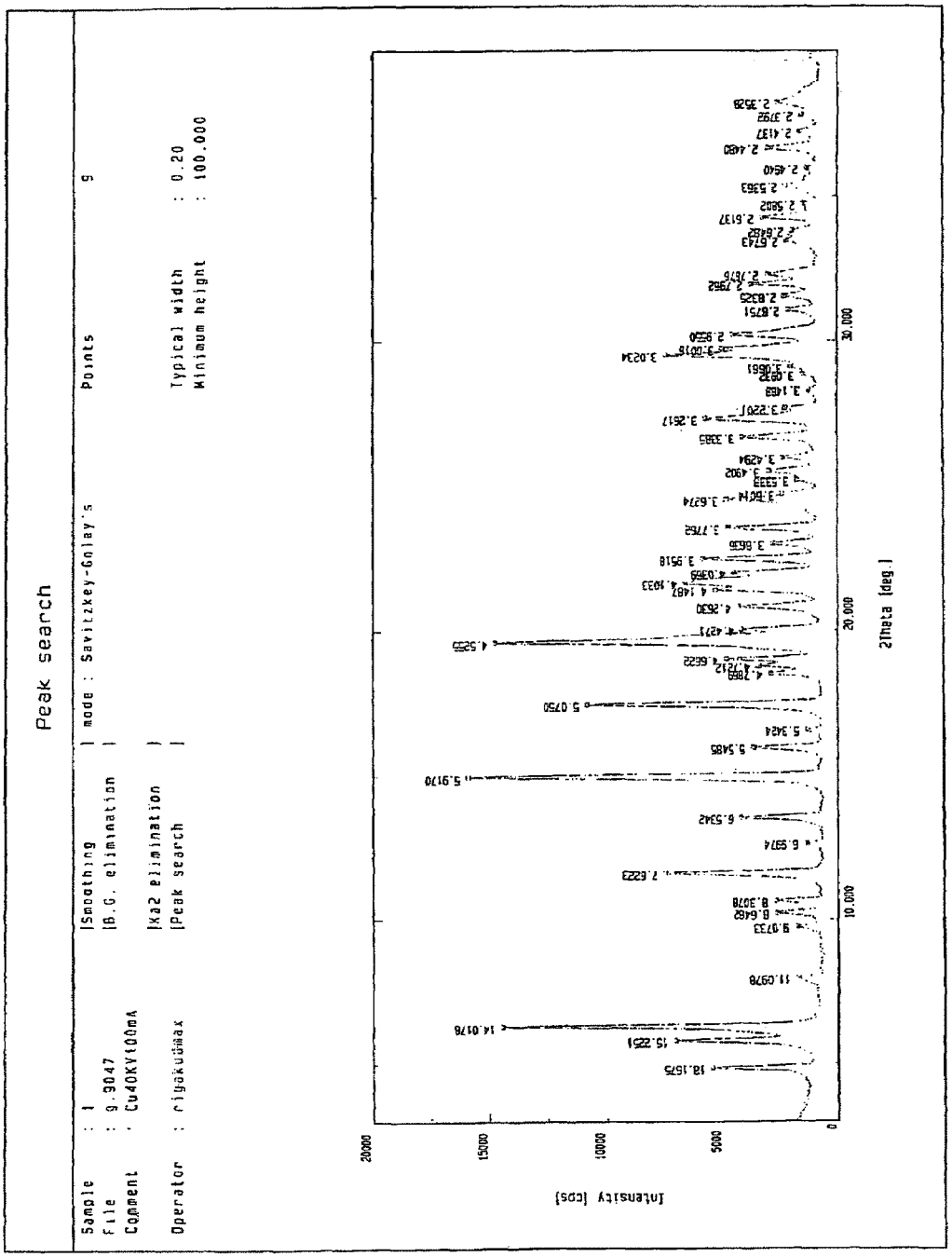
FIG. 2: X-ray powder diffraction pattern of cefazolin sodium pentahydrate.

The X-ray powder diffraction pattern of cefazolin sodium pentahydrate according to the present invention (Example 1) was shown in FIG. 2, wherein characteristic peaks occurred at 4.8, 5.8, 6.3, 11.6, 13.5, 14.9, 15.9, 17.4, 18.7, 19.0, 19.6, 20.0, 20.8, 21.4, 27.3, 29.5 (degrees 2θ/), and so on.

Figure 4:
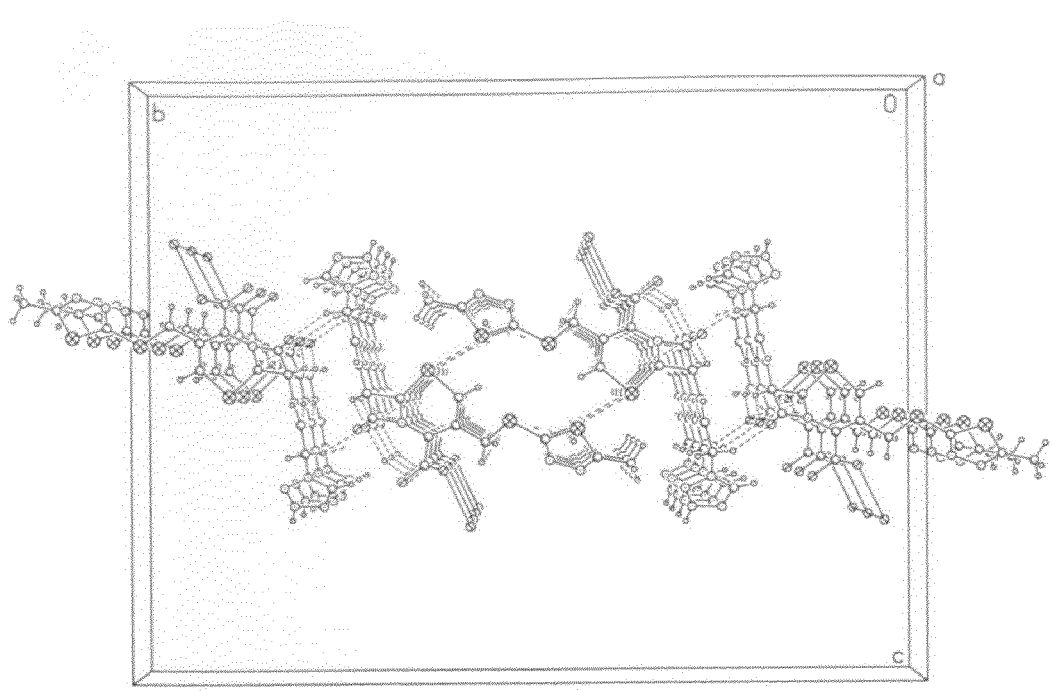
FIG. 4: Chart of accumulation of cefazolin sodium pentahydrate crystal cell in the direction of a axis.

FIG. 4 showed the chart of accumulation of cefazolin sodium pentahydrate crystal cell according to the present invention (Example 1) in the direction of a axis, measured by single crystal X-ray diffraction scanner, and the chart of accumulation was obtained by shelx software program analysis.

Figure 5:
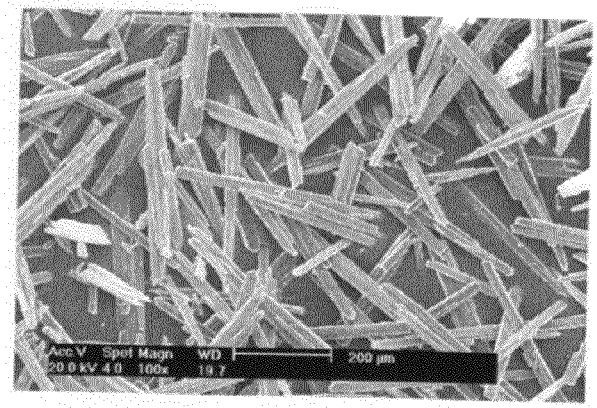
FIG. 5: Photograph of scanning electron microscope of cefazolin sodium pentahydrate product (100 times enlarged).

FIG. 5 showed the photographs of scanning electron microscope of cefazolin sodium pentahydrate product. The product obtained in Example 1 was analyzed and characterized by X-650 type scanning electron microscope produced by Japan Hitachi Company to obtain scanning electron microscope photographs.

The infrared adsorption spectrum of cefazolin sodium pentahydrate according to the present invention had characteristic absorption peaks at $3432(\pm5)cm^{-1}$, $3287(\pm5)cm^{-1}$, $1761(\pm5)cm^{-1}$, $1667(\pm5)cm^{-1}$, $1599(\pm5)cm^{-1}$, $1540(\pm5)cm^{-1}$, $1389(\pm5)cm^{-1}$, $1239(\pm5)cm^{-1}$, and $1184(\pm5)cm^{-1}$ and so on, measured by infrared spectrophotometry (Chinese Pharmacopoeia 2000 Edition 2 Section, Annex IVC), pH was 4.8-6.3, and water content was 13.0-16.0%.

The results of the products obtained in Examples 2 and 3 were substantially consistent with the results mentioned above.

DSC analytic results showed that cefazolin sodium pentahydrate according to the present invention (Example 2) had two dehydration peaks at a temperature elevating speed of 5° C./min, the dehydration temperature was 93(±5)° C. and 98(±5)° C.; cefazolin sodium directly decomposed without a melting adsorption peak, and the decomposition temperature was 193(±5)° C., the decomposition heat was −56(±5)kJ/mol. The results of the products obtained in Examples 1 and 3 were substantially consistent with the results mentioned above.

The present invention discloses the structure of cefazolin sodium pentahydrate crystal and a method for assembly and preparation of crystal molecule. According to the contents described in the present application, those skilled in the art can achieve the present invention by appropriately altering raw materials, technological parameters, and structural designs. The product and method of the present invention were described in the preferred examples. Those skilled in the art can obviously achieve the technology of the present invention by modifying or appropriately altering and combining the method and product described in the present invention without digressing from the contents, essences and scopes of the present invention. It should be specifically pointed out that all similar substitutions and alterations are obvious for those skilled in the art. They are all regarded to be included in the protection scope of the present invention.

What is claimed:

1. A method for preparing cefazolin sodium pentahydrate crystal comprising: adding 1-20 parts of a solvent to a reactor equipped with a jacket; adding 1 part of cefazolin acid and sodium salt in a molar ratio of about 1:1 to provide a reaction solution; heating until the reaction solution is clear; adjusting pH to 3-9; upon the completion of the reaction, transferring the liquid to a crystallizer equipped with a jacket; cooling in water bath; adding crystallization additives; holding for 0.3-4 hours at 0.8-2.5 atmospheric pressure; cooling at the temperature range of 0° C.-70° C., adding 3-15 parts of an antisolvent, filtering, washing with a detergent, and drying to provide cefazolin sodium pentahydrate.

2. A cefazolin sodium pentahydrate crystal prepared according to the method of claim 1, characterized in that the crystal molecule contains five water molecules, orthorhombic system, space group of C222(1), in which sodium ion is bonded to the cefazolin molecule with a coordination bond, and wherein the crystal has a pH of 4.8-6.3, a water content of 13.0-16.0%, DSC measurement shows that it has two dehydration peaks, the dehydration temperature is 93($\pm$5)° C. and 98($\pm$5)° C., it directly decomposes without a melting adsorption peak, the decomposition temperature is 193($\pm$5)° C., and the decomposition heat is $-56(\pm5)$kJ/mol, and the X-ray powder diffraction pattern of the crystal has characteristic peaks selected from the group consisting of 4.8, 5.8, 6.3, 11.6, 13.5, 14.9, 15.9, 17.4, 18.7, 19.0, 19.6, 20.0, 20.8, 21.4, 27.3, and 29.5 (degrees 2θ).

3. The cefazolin sodium pentahydrate crystal according to claim 2, wherein the crystal has characteristic absorption peaks at 3432($\pm$5)cm$^{-1}$, 3287($\pm$5)cm$^{-1}$, 1761($\pm$5)cm$^{-1}$, 1667($\pm$5)cm$^{-1}$, 1599($\pm$5)cm$^{-1}$, 1540($\pm$5)cm$^{-1}$, 1389($\pm$5)cm$^{-1}$, 1239($\pm$5)cm$^{-1}$, and 1184($\pm$5)cm$^{-1}$.

4. The method according to claim 1, wherein the solvent is a mixture of water and at least one organic solvent, wherein the water content in the solvent is greater than 15%.

5. The method according to claim 4, wherein the organic solvent is selected from the group consisting of acetone, dichloromethane, chloroform, methanol, ethanol, isopropanol, butanol, ethyl ether, ethyl acetate, and butyl acetate.

6. The method according to claim 1, wherein the sodium salt is selected from the group consisting of sodium carbonate, sodium hydroxide, sodium acetate, trihydrated sodium acetate, sodium isocaprylate, sodium bicarbonate, sodium methoxide, sodium ethoxide and mixtures thereof.

7. The method according to claim 1, wherein the antisolvent is an oxygen-containing fatty hydrocarbon derivative selected from the group consisting of fatty acids, aliphatic alcohols, ketones and mixtures thereof.

8. The method according to claim 7, wherein the antisolvent is formic acid, acetic acid, methanol, ethanol, n-propanol, isopropanol, n-butanol, isobutanol, acetone, isobutyl ketone or methyl ethyl ketone.

9. The method according to claim 7, wherein the antisolvent is ethanol, isopropanol, n-butanol, acetone, isobutyl ketone or acetic acid.

10. The method according to claim 7, wherein the antisolvent is methanol and isopropanol, acetone and ethanol, acetone and acetic acid, isobutyl ketone and isopropanol, or n-propanol and formic acid with a ratio of 20:1 to 1:20.

11. The method according to claim 1, wherein the detergent is an oxygen-containing fatty hydrocarbon derivative selected from the group consisting of fatty acids, aliphatic alcohols, ketones and mixtures thereof.

12. The method according to claim 11, wherein the detergent is formic acid, acetic acid, methanol, ethanol, n-propanol, isopropanol, n-butanol, isobutanol, acetone, isobutyl ketone or methyl ethyl ketone.

13. The method according to claim 1, wherein the crystallization additive is an amino acid compound selected from the group consisting of lysine, serine, methionine, and leucine.

14. The method according to claim 13, wherein the amino acid compound is lysine or serine.

15. The method according to claim 1, wherein the amount of the crystallization additive present is 0.1-0.5 ppm.

* * * * *